United States Patent
Riegel

(10) Patent No.: US 9,500,735 B2
(45) Date of Patent: Nov. 22, 2016

(54) METHOD FOR CALIBRATING A CONDUCTIVITY MEASURING CELL

(75) Inventor: Harald Riegel, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 640 days.

(21) Appl. No.: 13/884,161

(22) PCT Filed: Nov. 9, 2011

(86) PCT No.: PCT/EP2011/069732
§ 371 (c)(1),
(2), (4) Date: May 8, 2013

(87) PCT Pub. No.: WO2012/062798
PCT Pub. Date: May 18, 2012

(65) Prior Publication Data
US 2013/0221986 A1    Aug. 29, 2013

(30) Foreign Application Priority Data

Nov. 9, 2010 (DE) .......................... 10 2010 060 465

(51) Int. Cl.
*G01R 35/00* (2006.01)
*G01N 27/06* (2006.01)
(Continued)

(52) U.S. Cl.
CPC .......... *G01R 35/005* (2013.01); *G01N 27/06* (2013.01); *G01R 27/22* (2013.01); *G01N 27/221* (2013.01); *G01R 27/2605* (2013.01); *G01R 35/00* (2013.01)

(58) Field of Classification Search
CPC .............. G01R 27/2605; G01R 35/00; G01R 35/005
(Continued)

(56) References Cited

U.S. PATENT DOCUMENTS

| 3,648,165 A | * | 3/1972 | Shawhan | G01R 27/2605 324/601 |
| RE30,007 E | * | 5/1979 | Steuer | G01N 33/49 324/442 |

(Continued)

FOREIGN PATENT DOCUMENTS

| CN | 101629925 A | 1/2010 |
| DE | 198 44 489 A1 | 3/2000 |

OTHER PUBLICATIONS

A.P. Washabaugh, A. Mamishev, Y. Du, and M. Zahn; Dielectric Measurements of Semi-insulating Liquids and Solids, Conference Record of the ICDL '96 12" International Conference on Conduction and Breakdown in Dielectric Liquids, Roma, Italy, Jul. 15-19, 1996, pp. 381-384.*

(Continued)

*Primary Examiner* — Patrick Assouad
*Assistant Examiner* — Christopher McAndrew
(74) *Attorney, Agent, or Firm* — Christopher R. Powers; PatServe

(57) ABSTRACT

The invention relates to a method for calibrating a conductivity measuring cell located in a measurement setup for determining conductivity of a liquid medium, especially very pure water, by means of two electrodes of predetermined area arranged in the liquid medium at a predetermined separation relative to one another, supplied with an alternating voltage and having a cell constant, which is predetermined by separation and electrode area and must be calibrated. In order to be able to determine the cell constant independently of calibration standards with predetermined conductivity and/or reference measurement cells, an electrical capacitance of the measuring cell is ascertained by means of an alternating voltage placed on the electrodes in a frequency range between 1 kHz and 1 MHz, following (Continued)

US 9,500,735 B2

Page 2 which the cell constant is determined from the ascertained capacitance and the permittivity of the liquid medium contained in the measuring cell.

10 Claims, 2 Drawing Sheets

(51) Int. Cl.
G01R 27/22 (2006.01)
G01R 27/26 (2006.01)
G01N 27/22 (2006.01)

(58) Field of Classification Search
USPC .......................................................... 324/601
See application file for complete search history.

(56) References Cited

U.S. PATENT DOCUMENTS

| 4,691,168 | A | | 9/1987 | Dzula | |
|---|---|---|---|---|---|
| 4,786,875 | A | * | 11/1988 | Carll | G01N 27/045 324/443 |
| 4,799,174 | A | * | 1/1989 | Kramer | G01F 23/0069 324/601 |
| 5,269,175 | A | * | 12/1993 | Chmiel | G01N 33/2888 324/675 |
| 6,323,689 | B1 | * | 11/2001 | Morishita | H01L 27/0251 257/355 |
| 6,369,579 | B1 | | 4/2002 | Riegel | |
| 7,584,061 | B2 | * | 9/2009 | Wilf | B01D 61/025 702/34 |
| 8,179,141 | B2 | | 5/2012 | Rajagopalan et al. | |
| 8,597,480 | B2 | * | 12/2013 | Hodges | C12Q 1/004 204/400 |
| 8,686,740 | B2 | * | 4/2014 | Morishima | H02N 2/025 324/601 |
| 2008/0111559 | A1 | * | 5/2008 | Choi | G01R 27/2641 324/601 |
| 2008/0296208 | A1 | * | 12/2008 | Ikeyama | B01D 61/025 210/87 |
| 2008/0297173 | A1 | | 12/2008 | Zhou et al. | |
| 2013/0037263 | A1 | * | 2/2013 | Cheung | E21B 47/10 166/250.01 |

OTHER PUBLICATIONS

S. Seitz et al., "Traceability of electrolytic conductivity measurements to the International Systems of Units in the sub mSm-1 region and review of models of electrolytic conductivity cells," Electrochimica Acta, Elsevier Science Publishers, Banking, GB, vol. 55, No. 22, Sep. 1, 2010 [retrieved on Jun. 25, 2010], pp. 6323-6331, XP027215820.

International Preliminary Report on Patentability dated Jan. 26, 2012, issued in Application No. PCT/EP2011/069732, in Rijswijk, the Netherlands.

International Preliminary Report on Patentability dated May 23, 2013, issued in Application No. PCT/EP2011/069732, in Geneva, Switzerland.

* cited by examiner

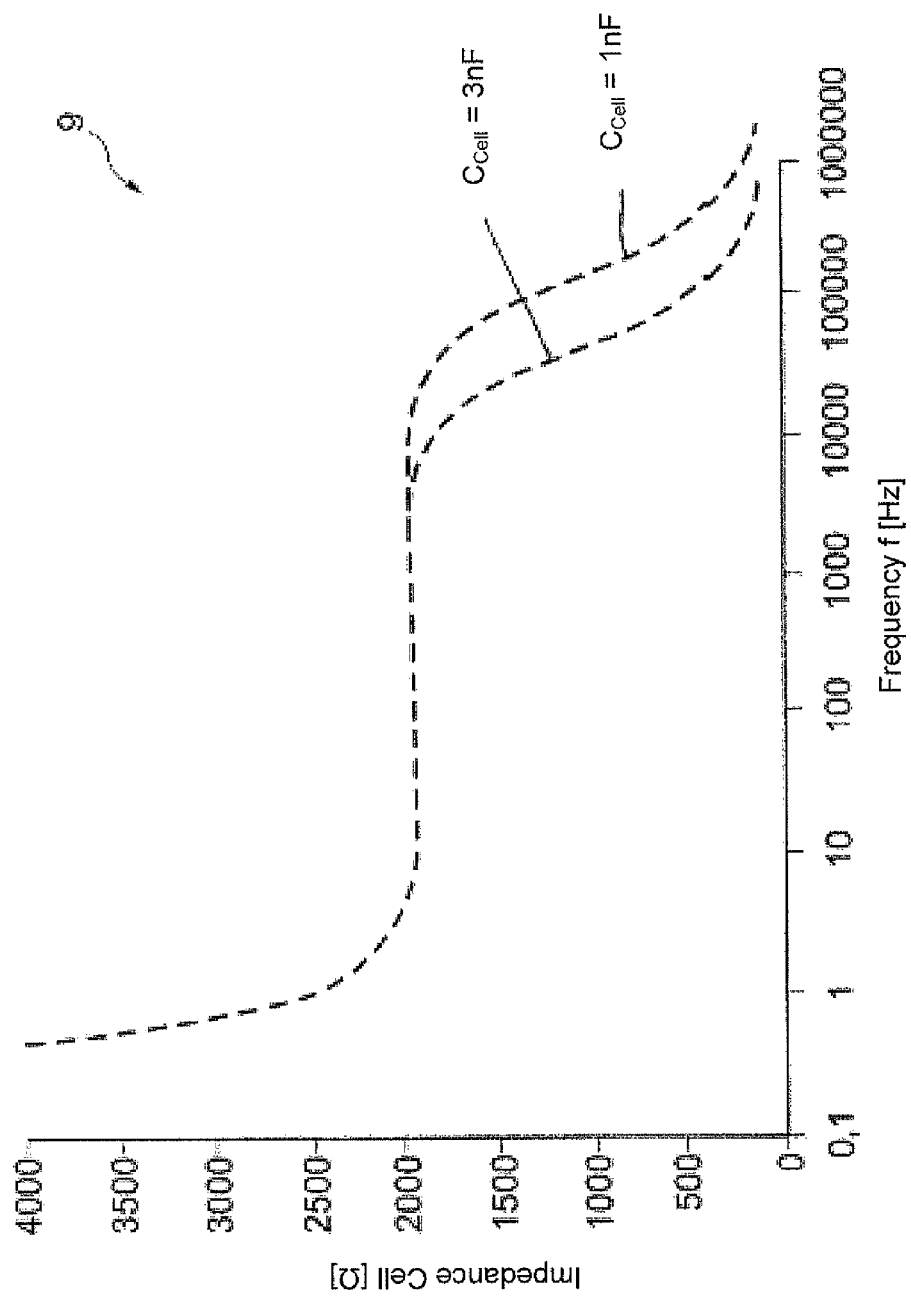

METHOD FOR CALIBRATING A CONDUCTIVITY MEASURING CELL

TECHNICAL FIELD

The invention relates to a method for calibrating a conductivity measuring cell located in a measurement setup for determining conductivity of a liquid medium, especially very pure water, by means of two electrodes of predetermined area arranged in the liquid medium at a predetermined separation relative to one another, supplied with an alternating voltage and having a cell constant, which is predetermined by separation and electrode area and must be calibrated.

BACKGROUND DISCUSSION

Measurement setups with conductivity measuring cells, which work according to the conductive measurement principle, wherein an alternating voltage is placed on electrodes directly in contact with a liquid medium and the electrical signal response proportional to the conductivity of the liquid medium is evaluated in a measuring device, are known from analytical and process measurements technology. German Patent DE 198 44 489 A1 discloses such a method for determining the electrical conductivity of liquids. The evaluation of the electrical signal response occurs, in such case, based on an equivalent circuit of the conductivity measuring cell, which is formed at least of a capacitor and a resistor connected in parallel therewith. In order especially to prevent disturbing polarization effects, the area of the electrodes and their separation from one another are matched on the measuring range of the conductivity measuring cell. This matching delivers a cell constant typical for each conductivity measuring cell. The cell constant is subject to production-related fluctuations and can change as a function of time, so that a measurement setup with such a conductivity measuring cell must, in given cases, be calibrated.

For this, the conductivity measuring cell is supplied with calibration liquids of predetermined conductivity and the resistance measured, for example, using an alternating voltage of 1 kHz. From the resistance, by means of the equivalent circuit, the cell constant is determined. For preventing measurement errors, the conductivity of the calibration liquids should lie in the range of the conductivities of the liquid medium to be measured. Especially in the case of liquid media with smaller conductivity, for example, very pure water, the providing of stable calibration liquids requires considerable effort. The application of reference cells, which precisely determine the conductivity of the liquid medium and thereby permit a calibrating of the cell constant by means of the so won conductivity of the liquid medium, just shifts the calibration effort by means of calibration liquids to the reference cell. Furthermore, in the case of installation in a measuring container, such as a vessel, additional container openings must be provided. The calibration is furthermore made difficult by the large temperature dependence of the conductivity measuring cell during a calibration by means of calibration liquids, which supplementally requires complex temperature measurement during the calibration with corresponding settling times of temperature especially between the conductivity measuring cell to be calibrated and the reference cell.

SUMMARY OF THE INVENTION

An object of the invention is, consequently, to provide a method for calibrating a conductivity measuring cell, which manages without calibration standards and reference cells.

The object is achieved by a method for calibrating a conductivity measuring cell located in a measurement setup for determining conductivity of a liquid medium, especially very pure water, by means of two electrodes of predetermined area arranged in the liquid medium at a predetermined separation relative to one another, supplied with an alternating voltage and having a cell constant, which is predetermined by separation and electrode area and must be calibrated, wherein an electrical capacitance of the measuring cell in the liquid medium is ascertained by means of an alternating voltage placed on the electrodes in a frequency range between 1 kHz and 1 MHz, preferably between 10 kHz and 1 MHz, following which the cell constant is determined from the ascertained capacitance and the permittivity of the liquid medium contained in the measuring cell.

By considering the conductivity measuring cell to be a capacitor, such as, depending on geometrical embodiment, a plate capacitor, a cylindrical capacitor or the like, in the case of which the liquid medium represents the dielectric with a certain permittivity, according to the invention, a relationship between the cell constant and the electrical capacitance, which is registered and calculated as signal response to the alternating voltage placed on the electrodes in a measuring device, can be produced, which is essentially independent of the conductivity of the liquid medium located between the electrodes in the conductivity measuring cell. Especially, for media of smaller conductivity, such as very pure water, and/or application of a liquid medium for calibration, whose conductivity, respectively dielectric constant, lies in the measuring range of the liquid medium to be measured—this is, as a rule, in the case of calibrations of a so-called in-line measurement, in any event, the situation—, the error of a change of the dielectric constant versus conductivity is essentially negligible. Therefore, neither complex measurements of the current conductivity by means of reference cells and calibrating the conductivity measuring cell based on the thereby ascertained conductivity nor complex treating of the conductivity measuring cell with difficultly manufactured calibration liquids, especially in inline applications, are needed. The permittivity is temperature dependent. The temperature dependence of the permittivity is, however, less than the temperature dependence of the conductivity. For increasing the accuracy, the capacitance measured value can be compensated by means of a supplementally registered, measured value of temperature. Except for the matching of the measuring device and, in given cases, the supply cable thereof to the measuring cell as regards the alternating voltages to be applied and their evaluation, no additional preliminary measures are needed for the measurement setup, so that the method can be performed in simple manner, cost effectively and with little complexity. The measuring is preferably performed in a liquid medium, which has a conductivity within the conductivity range of the medium to be measured. Especially advantageous is the performing of the measuring in the measured medium, since in such case there is no accessing of the installation of the conductivity measuring cell and the calibration can be performed in-situ, virtually between measurement operations. The calibration can, in such case, be performed automatically by the measuring device, since no manual procedures need to be performed by maintenance personnel. If the calibration fails, a corresponding status—or warning report can be output to the measuring device.

For ascertaining the cell constant $k$, for example, of a measuring cell with electrodes arranged parallel to one another, according to the invention, a relationship for the cell constant k is produced, which, in known manner, results from the electrode area A of the electrodes of the conductivity measuring cell, which, according to the equivalent circuit diagram, correspond to the plate surfaces of a capacitor, and the electrode separation I, which, according to the equivalent circuit, corresponds to the plate separation of the plates of a capacitor, as follows:

$$k = I/A. \quad (1)$$

The electrical cell capacitance $C_{Cell}$ of the conductivity measuring cell with the cell constant k results accordingly for a plate capacitor to be:

$$C_{Cell} = \epsilon_0 \epsilon_R / k \quad (2)$$

with permittivity $\epsilon_0$ of the vacuum and $\epsilon_R$ for the permittivity of the medium. For other electrode shapes and cell geometries, cell capacitance is determined correspondingly. It has been found, in such case, that the permittivity of the measuring cell over the conductivity values of the measuring range, especially in the case of very pure water, is sufficiently constant and the measurement error due to change of the dielectric constant dependent on a changing conductivity is significantly smaller compared with calibration defects in the case of the manufacture, supply and application of calibration liquids, temperature compensation of the measuring of conductivity and the like. The temperature dependence of the permittivity can be compensated by, for example, storing the ascertained or simulated temperature dependence in the measuring device and compensating by means of the temperatures registered by the temperature sensor present in the conductivity measuring cell.

By solving Equation (2) for the cell constant k, this can be calibrated in a simple manner using the directly registerable electrical capacitance. Proven to be especially advantageous, in such case, has been the application of an alternating voltage of 100 kHz on the electrodes. Dependent on the type of liquid medium to be measured, the structure of the conductivity measuring cell, the line length between measuring device and conductivity measuring cell, and, in given cases, additional parameters, the alternating voltage can be varied within a preferred frequency range from 10 kHz to 1 MHz. Of course, the frequency range can be expanded further, when particular requirements make its expansion advantageously appropriate.

In the case of significant line lengths and self-capacitance of the conductivity measuring cell, there can occur in the ascertained capacitance besides the cell capacitance $C_{Cell}$ a disturbance capacitance $C_S + C_R$ (FIG. 1), which is composed of a supply line capacitance $C_S$ and a residual capacitance $C_R$ of the conductivity measuring cell. According to the invention, this is separately determined and subsequently eliminated, for example, by subtracting it from the measured capacitance C. In an example of an embodiment of the method, the disturbance capacitance is ascertained by means of an alternating voltage placed on the electrodes in a frequency range between 10 kHz and 1 MHz in air and subtracted from the measured capacitance. For this, the conductivity measuring cell is measured empty. In such case, the determining of capacitance in a liquid medium and the disturbance capacitance do not need to unavoidably occur, in time, one after the other. Rather, preferably, once at start-up of the measurement setup or in greater time intervals than the calibrating of the cell constant, a determination of the disturbance capacitance can occur, whose value is stored in the measuring device and retrieved and processed for compensation of the intermediately occurring calibrations of the cell constant.

In air, the permittivity of the conductivity measuring cell becomes $\epsilon = 1$, compared with a permittivity of $\epsilon_R \approx 80$ in a liquid medium in the form of water, so that the cell capacitance $C_{Cell}$ needed for ascertaining the cell constant k according to Equation (2) solved for k is determined from measurements of the capacitance $C_A$ in air and the capacitance $C_W$ in water essentially according to the following formula:

$$C_{Cell} = (C_W - C_A) \frac{\epsilon_r}{\epsilon_r - 1} \quad (3)$$

In an alternative form of embodiment of the method, which can occur, for example, when the conductivity measuring cell cannot be deinstalled and/or correspondingly long supply lines are used as supply cable, the disturbance capacitance $C_S$ attributable essentially to the cable length of the connecting lines extending between the measuring device and the conductivity measuring cell can be determined by isolating the connecting lines from the conductivity measuring cell and connecting into the connecting line instead of the conductivity measuring cell a high-resistance resistor, for example, 100 kOhm to 10 MOhm, preferably 1 MOhm. Since this resistance is essentially capacitance-free, the measured capacitance is the supply line capacitance $C_S$. The supply line capacitance $C_S$ determined in this way is simply subtracted from the cell capacitance $C_{Cell}$. It has especially proven to be advantageous in the case of a conductivity measuring cell with significant supply line capacitance $C_S$, when this is ascertained, for example, by means of short, essentially capacitance-free cables or cables of negligible capacitance and an alternating voltage placed on the electrodes in air and such is used to correct the disturbance capacitance. In such case, upon one time determining of ascertained disturbance capacitances of, for example, less than 0.1 pF, further correction can be omitted. A determining of the cell capacitance $C_{Cell}$ of the conductivity measuring cell by means of determining the total capacitance $C_{withCell}$ and supply line capacitance $C_S$ of the connecting lines by means of a high-resistance resistor is made advantageously according to the following Equation (4):

$$C_{Cell} = C_{withCell} - C_S \quad (4)$$

For ascertaining a residual capacitance $C_R$ of the conductivity measuring cell, which residual capacitance registers the influence of the measurement setup of the conductivity measuring cell, measurement is made, especially exactly, by means of short cable by measuring the conductivity cell in liquid medium and in air. The residual capacitance $C_R$ is then calculated from the Equation (5) as follows:

$$C_R = \frac{\epsilon_r C_{0,A} - C_{0,W}}{\epsilon_r - 1} \quad (5)$$

In such case, $C_{0,W}$ represents the determined capacitance of the measurement setup with short cables of negligible capacitance in water and $C_{0,A}$ the determined capacitance of the measurement setup with short cables of negligible capacitance in air.

By means of the described method, advantageously, deviations of the cell constant over the operating time of the conductivity cell are compensated, deviations which result, for example, from changes of electrode shape, gap formation between embedded material of the electrodes and the electrode holders, and the like. If there occur on the electrodes contaminations, for example, fat films and the like, the geometric dimensions of the conductivity measuring cell and therewith the cell constant do not, indeed, change. However, a measurement is nevertheless corrupted as a result of electrode polarization. It has, consequently, proven to be advantageous to ascertain polarization of the electrodes by means of a phase shift of an applied alternating voltage in a frequency range between 1 kHz and 5 kHz. If polarization is detected, for example, by an exceeding of a predetermined threshold of the phase shift, a frequency of the applied alternating voltage of, for example, 1 kHz can be increased during a measurement of conductivity and/or during calibration. Alternatively or supplementally, a corresponding status—or warning report can be output in the measuring device.

BRIEF DESCRIPTION OF THE DRAWINGS

The invention will now be explained in greater detail based on the relationships of a conductivity measuring cell illustrated in the drawing, the figures of which show as follows:

FIG. 3 a diagram of impedance of the conductivity measuring cell versus frequency of an alternating voltage placed on the conductivity measuring cell.

DETAILED DISCUSSION IN CONJUNCTION WITH THE DRAWINGS

Figure 1:
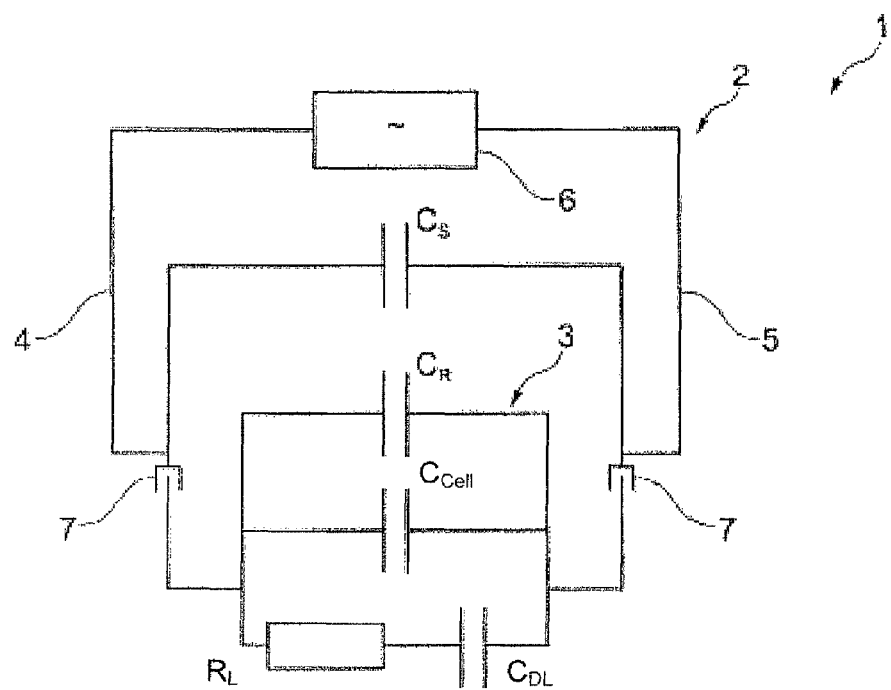
FIG. 1 an equivalent circuit diagram of a conductivity measuring cell in a measurement setup.

FIG. 1 shows the equivalent circuit diagram 1 of the measurement setup 2 with the conductivity measuring cell 3, which is connected by means of the plug connections 7 and the connecting lines 4, 5 with the measuring device 6. The conductivity measuring cell 3 is shown in the equivalent circuit diagram 1 as series connected solution resistance $R_L$ of the liquid solution and double layer capacitance $C_{DL}$ with cell capacitance $C_{Cell}$ connected parallel thereto. Responsible for measuring the conductivity by means of the electrodes of the conductivity measuring cell 3 is the solution resistance $R_L$, which shows the conductivity of the liquid medium and can be, for example, 4 kΩ, which, in the case of a cell constant of 0.01 cm$^{-1}$, corresponds to a conductivity of about 2.5 μS/m. The high double layer capacitance $C_{DL}$, which is very large compared with the cell capacitance $C_{Cell}$, is caused by charging—and charge reversal processes on the surfaces of the electrodes and amounts in the case of usual electrode areas to about 100 μF. The cell capacitance $C_{Cell}$ represents the electrical capacitance of the electrode construction with the electrode areas, their separation from one another and the dielectric material located therebetween during a measuring of the liquid medium to be measured, for example, water in the form of very pure water. Derived from the geometric dimensions of the electrodes and their separation from one another are both the cell constant of the conductivity measuring cell 3 as well as also, in connection with the applied dielectric, the permittivity of the component illustrated in the equivalent circuit diagram 1 as capacitor with the cell capacitance $C_{Cell}$. From the relationship illustrated in Equation (1) between the cell constant k and the cell capacitance $C_{Cell}$, which, in very pure water, can amount to about 1 nF, measurement of the cell capacitance $C_{Cell}$ can lead to the cell constant k without knowledge of the solution resistance $R_L$. The liquid medium enters into the determining of the cell constant exclusively in the form of the permittivity, whose change as a function of conductivity is negligible in the case of the predetermined measuring conditions.

As a result of the great differences between the double layer capacitance $C_{DL}$ and the cell capacitance $C_{Cell}$ amounting to several orders of magnitude, these can be distinguished almost disturbance freely by supplying the electrodes with alternating voltage of suitable frequency. As regards disturbances for the calibrating the cell constant by means of the cell capacitance $C_{Cell}$, cable capacitances in the form of the disturbance capacitances $C_S$ and self-capacitances of the conductivity measuring cell 3 in the form of the residual capacitance $C_R$ can be noticeable. These are eliminated by corresponding compensation measurements by measuring, for example, the conductivity measuring cell 3 in air, in which case the permittivity is significant lower and the disturbance capacitances are practically exclusively determined and, after their determination, subtracted out, in order to arrive at the cell capacitance. Alternatively, the plug connections 7 can be released and the connecting lines measured with connection of a high-resistance resistor. The residual capacitance $C_R$ is, in such case,—in so far that it is not negligible with, for example, 2 pF—measured with short cables.

Figure 2:
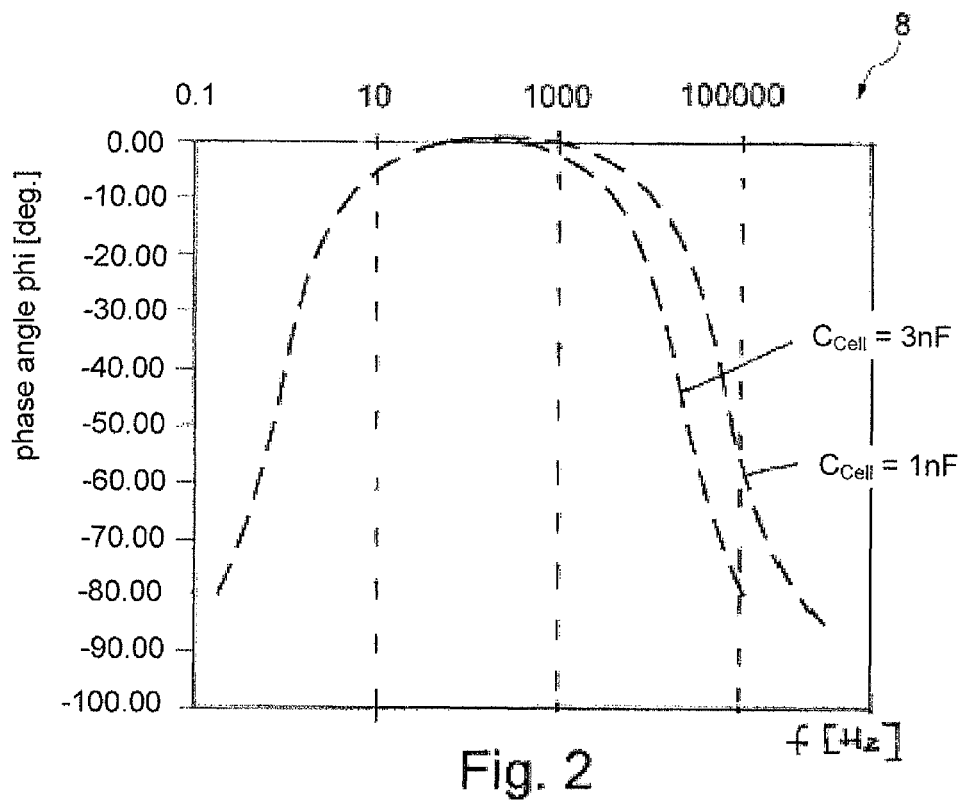
FIG. 2 a diagram of phase angle versus frequency of an alternating voltage placed on the conductivity measuring cell.

Graph 8 in FIG. 2 shows a simulated relationship between the phase angle phi ascertained in the measuring device 6 and the frequency f of the alternating voltage placed by the measuring device 6 on the electrodes of the conductivity measuring cell as an example for an assumed cell capacitance $C_{Cell}$ of 1 nF, respectively 3 nF. In the case of small frequencies up to 10 Hz, the influence of the double layer capacitance $C_{DL}$ is clear. In the region between 10 Hz and 1000 Hz, the influence of the solution resistance $R_L$ makes itself noticeable essentially without affecting phase angle, so that the measuring of conductivity is preferably performed in this frequency range.

In the case of frequencies greater than 1000 Hz, the influence of the cell capacitance $C_{Cell}$ can be evaluated. In this frequency range, thus, the determining of the cell capacitance can occur. Depending on the size of the cell constant, a suitable calibration frequency is preferably selected between 100 kHz and 1 MHz.

FIG. 3 shows a graph 9 of the impedance Z versus frequency of the alternating voltage placed on the electrodes of the conductivity measuring cell 3 of FIG. 1 in a simulation for two cell capacitances $C_{Cell}$, 1 nF and 3 nF. In such case, it is clear that the impedance Z in the case of frequencies greater than 10 kHz, especially greater than 100 kHz, depends on the cell capacitance $C_{Cell}$ and therewith can be evaluated for determining the cell constant.

The invention claimed is:

1. A method for calibrating a conductivity measuring cell located in a measurement setup for determining conductivity of a liquid medium, by means of two electrodes of predetermined area arranged in the liquid medium at a predetermined distance relative to one another, comprising the steps of:
supplying the electrodes with an alternating voltage and having a cell constant, which is predetermined by distance and electrode area and must be calibrated;
ascertaining an electrical capacitance of the measuring cell by means of the alternating voltage placed on the electrodes in a frequency range between 1 kHz and 1 MHz, following which; and determining the cell constant from a cell capacitance ($C_{cell}$), as ascertained from the measured capacitance and the permittivity of the liquid medium contained in the measuring cell;

wherein the cell constant is calibrated using the measured electrical capacitance and the permittivity of the liquid medium contained in the measuring cell.

2. The method as claimed in claim 1, further comprising the step of:

eliminating a disturbance capacitance ($Cs+C_R$) contained in a measured capacitance and caused by the measurement setup before determining the cell constant.

3. The method as claimed in claim 2, further comprising the step of:

ascertaining the disturbance capacitance ($Cs+C_R$) by means of the alternating voltage placed on the electrodes in a frequency range between 1 kHz and 1 MHz in air and in water and subtracted from the measured capacitance.

4. The method as claimed in claim 2, further comprising the step of:

ascertaining the supply line capacitance (Cs) by means of a high-resistance resistor connected to connecting lines of the measurement setup instead of the conductivity measuring cell and an alternating voltage in a frequency range between 1 kHz and 1 MHz and subtracted from the measured capacitance.

5. The method as claimed in claim 4, further comprising the step of:

ascertaining a residual capacitance ($C_R$) of the conductivity measuring cell by means of cables with negligible cable capacitance compared to the residual capacitance $C_R$ and an alternating voltage placed on the electrodes in air and used to correct the disturbance capacitance (Cs+CR).

6. The method as claimed in claim 2, further comprising the step of:

ascertaining the disturbance capacitance ($Cs+C_R$) independently of calibration cycles of the calibration and stored in a measuring device for eliminating capacitances during calibrations.

7. The method as claimed in claim 1, wherein:

an ascertained or simulated temperature dependence of the permittivity in the measuring device is stored and, by means of a temperature registered by a temperature sensor present in the conductivity measuring cell, used for compensating the capacitance measured value.

8. The method as claimed in claim 1, wherein:

the liquid medium lies during the calibration as regards its conductivity within a conductivity range to be measured.

9. The method as claimed in claim 1, further comprising the step of:

ascertaining a polarization of the electrodes by means of a phase shift of an applied alternating voltage in a frequency range between 1 kHz and 5 kHz.

10. The method as claimed in claim 9, further comprising the step of:

increasing frequency in the case of detected polarization, during measuring of conductivity and/or during calibration.

* * * * *